(12) United States Patent
Godefroidt et al.

(10) Patent No.: US 8,409,699 B2
(45) Date of Patent: Apr. 2, 2013

(54) BREATHING SHEET MATERIAL HAVING AN ADHESIVE COATING LAYER AND MANUFACTURING METHOD THEREFOR

(75) Inventors: Frank Godefroidt, Gent (BE); Joost Van Osnabrugge, Tessenderlo (BE); Tom Vets, Tessenderlo (BE); Raymond Vanstraelen, Tessenderlo (BE)

(73) Assignees: Reskin Medical NV, Tessenderlo (BE); Hogeschool Gent, Gent (BE)

( * ) Notice: Subject to any disclaimer, the term of this patent is extended or adjusted under 35 U.S.C. 154(b) by 409 days.

(21) Appl. No.: 12/674,167

(22) PCT Filed: Aug. 19, 2008

(86) PCT No.: PCT/EP2008/060840
§ 371 (c)(1),
(2), (4) Date: Feb. 19, 2010

(87) PCT Pub. No.: WO2009/024570
PCT Pub. Date: Feb. 26, 2009

(65) Prior Publication Data
US 2011/0097531 A1    Apr. 28, 2011

(30) Foreign Application Priority Data

Aug. 20, 2007 (EP) .................................. 2007058618
Feb. 19, 2008 (EP) ..................................... 08151599

(51) Int. Cl.
*B32B 3/26* (2006.01)
*B32B 5/14* (2006.01)
*B32B 3/00* (2006.01)
*B32B 7/12* (2006.01)

(52) U.S. Cl. ............... 428/304.4; 428/308.4; 428/313.3; 428/317.1; 428/317.3; 428/317.5

(58) Field of Classification Search ............... 428/304.4, 428/308.4, 313.3, 317.1, 317.3, 317.5
See application file for complete search history.

(56) References Cited

U.S. PATENT DOCUMENTS 3,438,371 A * 4/1969 Mack et al. ..................... 602/47
4,838,253 A   6/1989 Brassington et al.
(Continued)

FOREIGN PATENT DOCUMENTS

EP    0251810 A2    1/1988
EP    0261167 A1    3/1988
(Continued)

OTHER PUBLICATIONS

International Search Report dated Feb. 25, 2009 pertaining to International application No. PCT/EP2008/060840.

*Primary Examiner* — Victor Chang
(74) *Attorney, Agent, or Firm* — Dinsmore & Shohl LLP

(57) ABSTRACT

The invention relates to a breathing adhesive sheet material comprising a sheet layer having apertures and an adhesive coating layer with apertures corresponding to at least part of the apertures of said sheet layer, provided on one side of said sheet layer having apertures, wherein said apertures in said adhesive coating layer constitute portions of a substantially continuous adhesive coating layer separated there from by remaining adhered to a protective sheet layer upon removal thereof. The invention also relates to a composite sheet material comprising such adhesive sheet material with a removable protective sheet layer provided to separate portions from the continuous adhesive layer upon separation thereof from the adhesive sheet material. The invention also relates to a method for manufacturing such an adhesive sheet material comprising the steps of applying a layer of uncured adhesive material to a sheet layer having apertures and a layer of protective sheet material, and submitting the sheet layer having apertures, the layer of protective sheet material and the layer of uncured adhesive material to a curing operation, thereby causing the layer of adhesive material to preferentially adhere to the sheet layer having apertures outside the apertures, and to adhere to the protective sheet layer at said apertures.

12 Claims, 4 Drawing Sheets

U.S. PATENT DOCUMENTS

Figure 1:
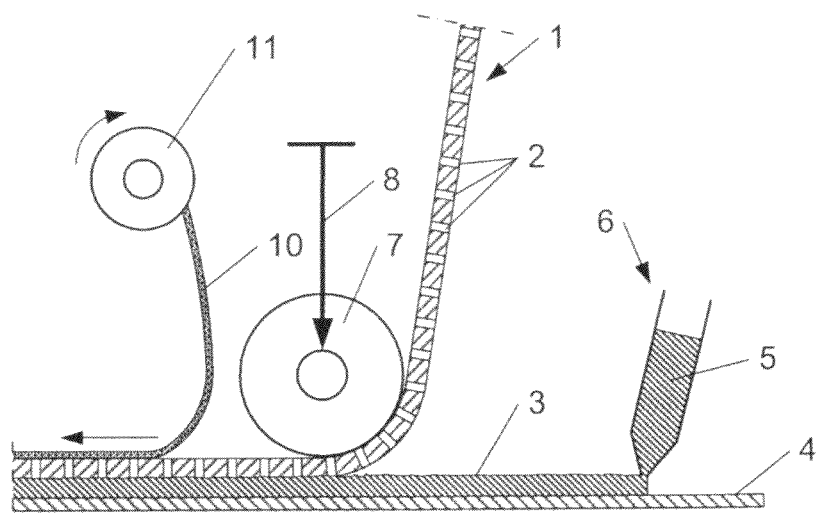

| | | |
|---|---|---|
| 5,340,363 A | 8/1994 | Fabo |
| 5,891,076 A | 4/1999 | Fabo |
| 5,919,476 A | 7/1999 | Fischer et al. |
| 2003/0007999 A1 | 1/2003 | Blatchford et al. |

FOREIGN PATENT DOCUMENTS

| | | |
|---|---|---|
| EP | 0300620 A1 | 1/1989 |
| EP | 0409587 A1 | 1/1991 |
| EP | 0497607 A1 | 8/1992 |
| EP | 0633757 A1 | 1/1995 |
| EP | 0633758 A1 | 1/1995 |
| EP | 0782457 A1 | 7/1997 |
| EP | 0922130 A1 | 6/1999 |
| EP | 1175527 A1 | 1/2002 |
| GB | 2192142 A | 1/1988 |
| WO | 93/19709 A1 | 10/1993 |
| WO | 93/19710 A1 | 10/1993 |
| WO | 02/45698 A2 | 6/2002 |
| WO | 03/011352 A1 | 2/2003 |
| WO | 2004/082935 A1 | 9/2004 |
| WO | 2005/048911 A2 | 6/2005 |

\* cited by examiner

BREATHING SHEET MATERIAL HAVING AN ADHESIVE COATING LAYER AND MANUFACTURING METHOD THEREFOR

The invention relates to the general field of protective sheet material having an adhesive layer, such as, in particular, adhesive protective sheet materials intended for application to the skin.

Such protective sheet materials are known as such, for instance for therapeutic applications such as the treatment and/or rehabilitation of scar tissue, burn wounds, etc.

Reference can in this respect be made for instance to U.S. Pat. No. 4,838,253, European patents EP 0 261 167 (U.S. Pat. No. 5,340,363), EP 0 633 757, EP 0 633 758, EP 0 782 457 (U.S. Pat. No. 5,891,076) and EP 0 409 587, and publications WO 02/45698 and WO 2005/048911.

Typical commercial products comprise Safetac® products of MÖLNLYCKE, ScarBan® products of TRICOLAST, and COMPEED products of Johnson & Johnson, etc.

According to U.S. Pat. No. 4,838,253 the material may involve a dressing of tacky silicone gel on one surface and a non tacky silicone elastomer on the other surface.

EP 0 261 167 (U.S. Pat. No. 5,340,363) discloses a liquid permeable sheet material comprising one or more sheets of apertured material coated with a sufficient amount of tacky silicone gel to effectively encapsulate the sheet(s) but insufficient to occlude the apertures.

EP 0 782 457 (U.S. Pat. No. 5,891,076) relates to a scar dressing material comprising a flexible carrier sheet embedded within a silicone gel such that the gel forms continuous layers on both sides.

WO 02/45698 discloses a silicone gel sheet comprising an elastic fabric carrying, on the surface contacting the skin, a tacky silicone gel elastomer that does not permeate the fabric, being thus uncoated on the exterior surface.

WO 2005/048911 discloses a similar product involving a breathable PU layer on the surface which is not provided with a silicone layer.

EP 0 409 587 discloses a thin self-adhesive dressing for the prevention/treatment of skin friction blisters, comprising a film coated with a pressure sensitive adhesive, whereas said film consists of an elastomeric film material with a specific thickness, specific moisture transmission properties, specific texture properties and specific friction properties.

In many applications of adhesive protective sheet materials intended for application to the skin, it is rather essential that the adhesive sheet material has good "breathability" properties, or, in other words, that the adhesive sheet material involves sufficient apertures in the adhesive layer to allow proper breathing of the skin.

Manufacturing protective materials comprising a sheet layer having apertures and an adhesive coating layer on one side of said sheet layer, with apertures corresponding to at least part of the apertures of said sheet layer, is however a fundamental problem in the art.

Known approaches to achieve such apertures in an adhesive coating layer involve techniques which blow a flow of air through an adhesive coating layer during its application on a fabric material with apertures.

EP 0 922 130 thus discloses an "open" fabric material, in strip shape, comprising a friction-generating layer which "follows" the open structure of the fabric material, such as for suspender-less socks and stockings.

WO 2004/082935 discloses a similar "open" fabric material capable of adhering to the skin, comprising a cured adhesive silicone layer which "follows" the open structure of the fabric material, whereas a barrier layer between the fabric and the silicone layer prevents absorption of the silicone into the fabric.

Other approaches involve the use of specific (hydrophilic) adhesive resins for application on specific ("net") substrates to leave a majority of apertures in the substrate unoccluded, as disclosed in EP 0 497 607, or the use of specific liquid pregel mixtures for an adhesive coating, for application on specific web substrates provided with a coating having a surface energy which is lower than that of the liquid pregel mixtures, as disclosed in EP 1 175 527.

The present invention now proposes a totally innovative approach to the problem of manufacturing sheet materials comprising a sheet layer having apertures and an adhesive coating layer, provided on one side of said sheet layer, with apertures corresponding to at least part of the apertures of said sheet layer.

This objective of the invention is achieved by providing a composite sheet material comprising a sheet layer having apertures (or, in other words, a "breathing" sheet layer), an adhesive coating layer on said sheet layer having apertures, and a removable protective sheet layer adhering at least partially to said adhesive coating layer, in which said adhesive coating layer consists of a substantially continuous layer with portions of said substantially continuous layer, corresponding to at least part of the apertures of said sheet layer, provided to separate from said continuous layer and to adhere to said protective sheet layer upon separation of said protective sheet layer from said sheet layer having apertures with the remaining portions of said adhesive coating layer remaining adhered to said sheet layer having apertures.

According to a first embodiment of the invention, this composite sheet material may more specifically comprise a substantially continuous adhesive coating layer provided on one side of said sheet layer having apertures and a removable protective sheet layer adhering to said adhesive coating layer on the side remote from said sheet layer having apertures, whereas said portions of said substantially continuous adhesive coating layer, corresponding to at least part of the apertures of said sheet layer, are provided to separate from said continuous adhesive coating layer and to adhere to said protective sheet layer upon separation of said protective sheet layer from said sheet layer having apertures.

According to a second embodiment of the invention, this composite sheet material may more specifically comprise a substantially continuous adhesive coating layer provided on one side of said sheet layer having apertures and a removable protective sheet layer on the opposite side of said sheet layer having apertures, adhering partially to said adhesive coating, through portions of said substantially continuous adhesive coating layer corresponding to at least part of the apertures of said sheet layer, contacting said protective sheet layer, whereas said portions of said substantially continuous adhesive coating layer corresponding to at least part of the apertures of said sheet layer, are provided to separate from said continuous layer and to adhere to said protective sheet layer upon separation of said protective sheet layer from said sheet layer having apertures.

In the context of this invention the expression 'adhesive coating layer' very broadly refers to any type of coating layer which is adhesive/tacky towards an arbitrary kind of surface, such as in particular towards a skin surface (more in particular a human or animal skin), including layers of a tacky therapeutic gel materials (such as a silicone gel/silicone gel elastomer materials, adhesives based on natural or synthetic rubbers, acryl polymers, rubber/acrylate adhesives, etc.).

Similarly the expression 'sheet layer having apertures' broadly refers to any type of fabric, film or sheet material comprising apertures, holes, openings, allowing good breathability of said sheet layer (including elastic fabric materials (knitted, woven or non woven), so called "plastic netz" materials, "punctured", "perforated" or "apertured" plastic films, sheets of polymeric foam with open cells, non woven materials in general, breathable elastic materials in general, perforated or non perforated breathable polyurethane sheet materials, extruded "netz" materials, extruded films, and the like).

The adhesive layer (with apertures corresponding to at least part of the apertures of the sheet layer) of the materials according to the invention may, depending on their specific end use, cover the total surface of (the sheet layer/of a piece of the sheet layer of) said materials, or, alternatively, only a part/specific parts of such materials.

The adhesive layer may very suitably be applied/be present in a ratio of 10-500 g/m², most suitably in a ratio of 10-300 g/m² (depending also on the nature of the protective sheet layer material (or "carrier" material/"transfer paper" or "transfer film" material), with most suitably a final thickness between 50µ and 1000µ, most preferably between 100µ and 500µ.

The used sheet layers having apertures are preferably rather thin, with preferred thicknesses (without adhesive coating) ranging from about 0.01 mm to about 2 mm, most preferably from 0.02 to 0.6 mm.

The protective sheet material (or "carrier" material/"transfer paper" or "transfer film" material, consisting of paper, polyester or any other carrier material) has a "thickness" ranging from 0.05 mm to about 1 mm, most preferably from 0.1 to 0.6 mm, or (as more generally expressed in sheet material art) a weight per area unit in the order of 5-100 g/m²).

Preferably low thicknesses of the protective sheet are selected in order to achieve the lowest possible overall weight of the finished composite sheet product.

The invention also specifically relates to an adhesive sheet material comprising a sheet layer having apertures (or, in other words, a "breathing" sheet layer), and an adhesive coating layer with apertures corresponding to at least part of the apertures of said sheet layer, provided on one side of said sheet layer having apertures, (as such, without removable protective sheet layer), wherein said apertures in said adhesive coating layer constitute portions of a substantially continuous adhesive coating layer provided on said sheet layer having apertures, separated from said continuous adhesive coating layer by remaining adhered to a protective sheet layer temporarily provided to at least said portions of said substantially continuous adhesive coating layer, upon removal of said protective sheet layer.

According to a first embodiment of this adhesive sheet material according to the invention, said apertures in said adhesive coating layer more specifically constitute portions separated from said substantially continuous adhesive coating layer upon removal of said protective sheet layer temporarily provided to said substantially continuous adhesive coating layer.

According to a second embodiment of this adhesive sheet material according to the invention, said apertures in said adhesive coating layer constitute portions of said substantially continuous adhesive coating layer separated there from through said apertures of said sheet layer, upon removal of said protective sheet layer temporarily provided to the side of said sheet layer remote from said substantially continuous adhesive coating layer but in contact with said portions of said continuous adhesive coating layer.

The invention also specifically relates to a method for manufacturing composite sheet materials, respectively adhesive sheet materials according to the invention, as defined above, comprising the steps of applying a layer of uncured adhesive material to a sheet layer having apertures and a layer of protective sheet material, whereas said adhesive material when cured and said sheet material show a first adherence capacity $A_1$ towards each other, and said sheet layer having apertures and said adhesive material when cured show a second adherence capacity $A_2$ towards each other, said second adherence capacity $A_2$ being greater than said first adherence capacity $A_1$, and submitting said sheet layer having apertures, said layer of protective sheet material and said layer of uncured adhesive material to a curing operation for said adhesive material, thereby causing said layer of adhesive material to preferentially adhere to said sheet layer having apertures outside said apertures, and to adhere to said protective sheet layer at least at part of said apertures, thus causing said composite to comprise a removable protective sheet layer which upon removal leaves a sheet material comprising a sheet layer having apertures and an adhesive coating layer with apertures corresponding to at least part of the apertures of said sheet layer, provided on one side of said sheet layer having apertures.

Curing of the uncured adhesive layer is preferably carried out in an oven with air in the range of 60-200° C.

According to a first embodiment of this method according to the invention, the method more specifically comprises applying a layer of uncured adhesive material to a layer of protective sheet material, applying a sheet layer having apertures onto said layer of uncured adhesive material, submitting the obtained composite of said layer of protective sheet material, said layer of uncured adhesive material and said sheet layer having apertures to a curing operation for said adhesive material.

According to a second embodiment of the method according to the invention, the method more specifically comprises applying a layer of uncured adhesive material onto a composite sheet comprising a sheet layer having apertures and a layer of protective sheet material, on the side of said sheet material having apertures, in such way that the uncured adhesive material reaches to said layer of protective sheet material through said apertures in said sheet material having apertures, and submitting the obtained composite of said layer of protective sheet material, said layer of uncured adhesive material and said sheet layer having apertures to a curing operation for said adhesive material.

As indicated the adhesive sheet material according to the invention should have good breathability, as expressed by an air permeability (according to ISO 9237-2) of at least 50 l/min·dm² (~85 l/m²·s), preferably at least 250 l/min·dm² (~420 l/m²·s), and/or as expressed by a "high" vapour permeability corresponding to a moisture vapour transmission rate (according to ASTM E96) of at least 200 g/m²/day, preferably of at least 1000 g/m²/day), or to an evaporation rate through the material of at least 30% per 24 hours (at a relative humidity of 50% and a temperature of 32° C.).

The breathability of the adhesive sheet material according to the invention can also be expressed by a permeating resistance parameter "R" as measured, for instance, by means of a KES-F8 Air Permeability Tester as marketed by KATO TECH CO. LTD.

Typically, preferred sheet materials according to the invention have a permeating resistance parameter "R" in the range below 1 KPa·s/m, preferably as low as 0.01 KPa·s/m.

The sheet layer having apertures/holes/openings preferably has an opening area of at least 2% of the sheet layer area, with the adhesive coating layer having corresponding openings of at least 2% of its layer area.

The material of the sheet layer having apertures (or "breathing" sheet layer) has openings or holes/apertures obtained either during the fabrication of the sheet layer itself (by "weaving in" or "knitting in" apertures (eyelets), or any other technique for "manufacturing in" the apertures into the fabric/film/"netz" material), or during a perforation/puncturing step subsequent to the fabric/film/"netz" manufacturing, before the step of providing the adhesive coating layer to the sheet layer.

An optional aspect of the sheet layer having apertures may consist in a bi-elastic behaviour (same or different elasticity in longitudinal and in transverse directions) of the sheet layer, so that a piece of adhesive sheet material according to the invention can optimally follow the body part to which it is applied/adhered (with elasticity up to 150% and more).

According to a further preferred feature of the invention, the adhesive sheet material may very suitably comprise from 20 to 500 apertures per $dm^2$, with an opening area of at least 2-20% of the sheet material area.

According to a further feature of the invention the adhesive coating layer may for instance consist of a silicone gel elastomer coating, resulting from a two component silicone system for skin adhesion, adequately formulated in appropriate proportions and cured to provide the proper skin tackiness.

Such preferred silicone systems are commonly known in the art (reference is made in this respect to U.S. Pat. No. 5,891,076 mentioned here above) and commercially available for various applications involving adhesion directly on the skin (such as in particular for breast prosthesis application and for the treatment of burns/fire injuries, etc.), and referred to for instance in patent documents GB-A 2 192 142, EP-A 0 399 520, EP-A 0 251 810 and U.S. Pat. No. 5,919,476.

The essence in the context of the present invention is optimal skin friendliness, optimal skin adhesion/skin release properties, and proper balance between the adherence capacity $A_1$ of the adhesive material when cured towards the protective sheet material, the adherence capacity $A_2$ of the adhesive material when cured towards the sheet layer having apertures, and the inherent internal cohesion of the adhesive coating layer.

According to the invention, this specific balance between the adherence capacity $A_1$ of the adhesive material when cured towards the protective sheet material and the adherence capacity $A_2$ of the adhesive material when cured towards the sheet layer having apertures may be achieved by balancing the formulation of the adhesive coating composition, the choice of the sheet layer material and possible finishing products thereon, the thickness of the applied uncured adhesive coating layer, the choice of the protective sheet layer material, and any special preparation step of said protective sheet material (or carrier material/transfer layer/transfer "paper", as set forth in more detail in the disclosure of the manufacturing process, further below) to influence its adherence properties.

Suitable silicone adhesive systems are for instance available from WACKER Silicones (in particular under the reference "ELASTOSYL® P 7010") and from DOW CORNING (in particular under reference "DOW CORNING® 3631").

The proportions of the two components of the silicone system will depend on the required tackiness and flexibility of the coating, and the relative adherence capacities $A_1$ and $A_2$, in relation with the applied curing times, curing temperatures, etc.

The adhesive sheet material according to the invention, with a (uncoated) sheet layer having apertures having a thickness between 0.01 mm and 2 mm, preferably between 0.02 mm and 0.6 mm (such as sheet layers with a thickness of approximately 0.5 mm weighing around 185 $g/m^2$ or sheet layers with a weight per area unit of 36 $g/m^2$), and with an adhesive coating layer having a thickness between 50μ and 1000μ, preferably between 100μ and 500μ (and/or corresponding to a coating layer of approximately 50-500 $g/m^2$), such as a silicone gel layer of ~200 $g/m^2$, thus involves an overall thickness (sheet layer+adhesive coating layer) between 0.15 and 2 mm (between 150μ and 2000μ) and/or an overall specific weight of approximately 70 to 850 $g/m^2$, such as in particular an adhesive sheet material (sheet layer+adhesive coating layer) with a thickness of approximately 0.8 mm (800μ) and a weight of approximately 385 $g/m^2$.

The elastic property of the fabric used for the adhesive sheet materials according to the invention constitutes an interesting advantage in the specific use of said materials in sports and/or medical applications, in view of the muscle compression which the sheet material can provide.

The method, according to the invention, for manufacturing the adhesive sheet materials according to the invention and the composite sheet materials with a protective sheet layer, according to the invention, may be carried out as a so called "transfer method" or, alternatively, as a so called "direct" method.

Figure 2:
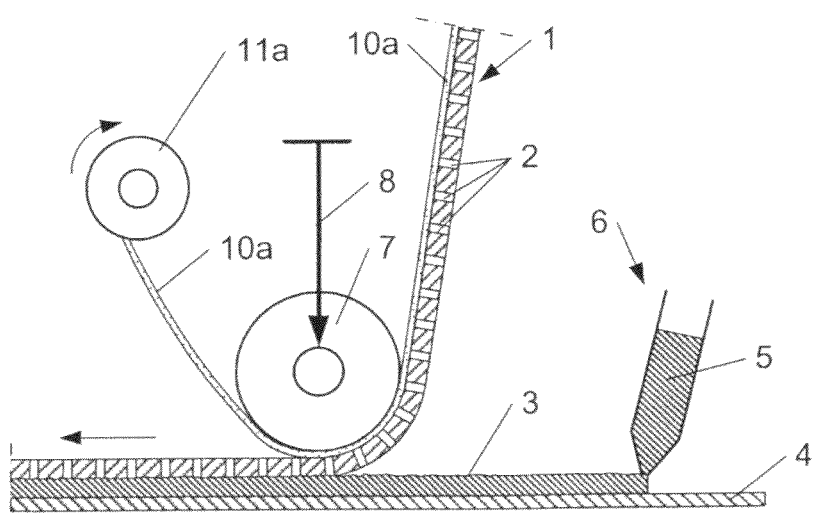
Figure 3:
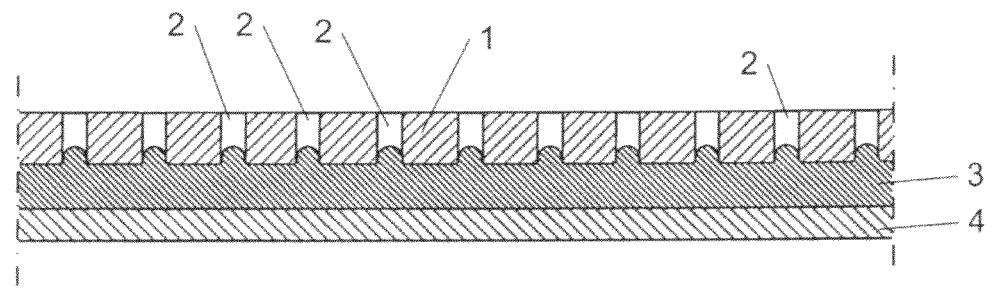
Figure 4:
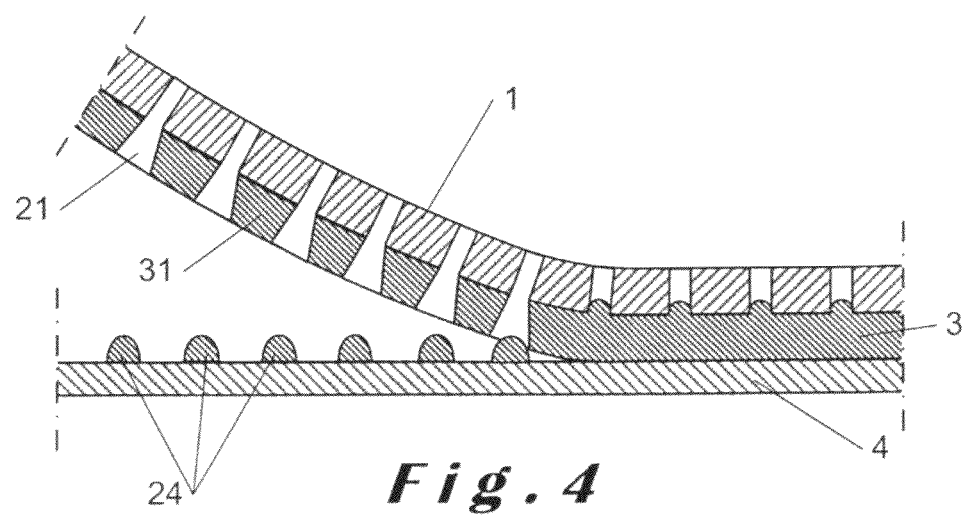
Figure 5:
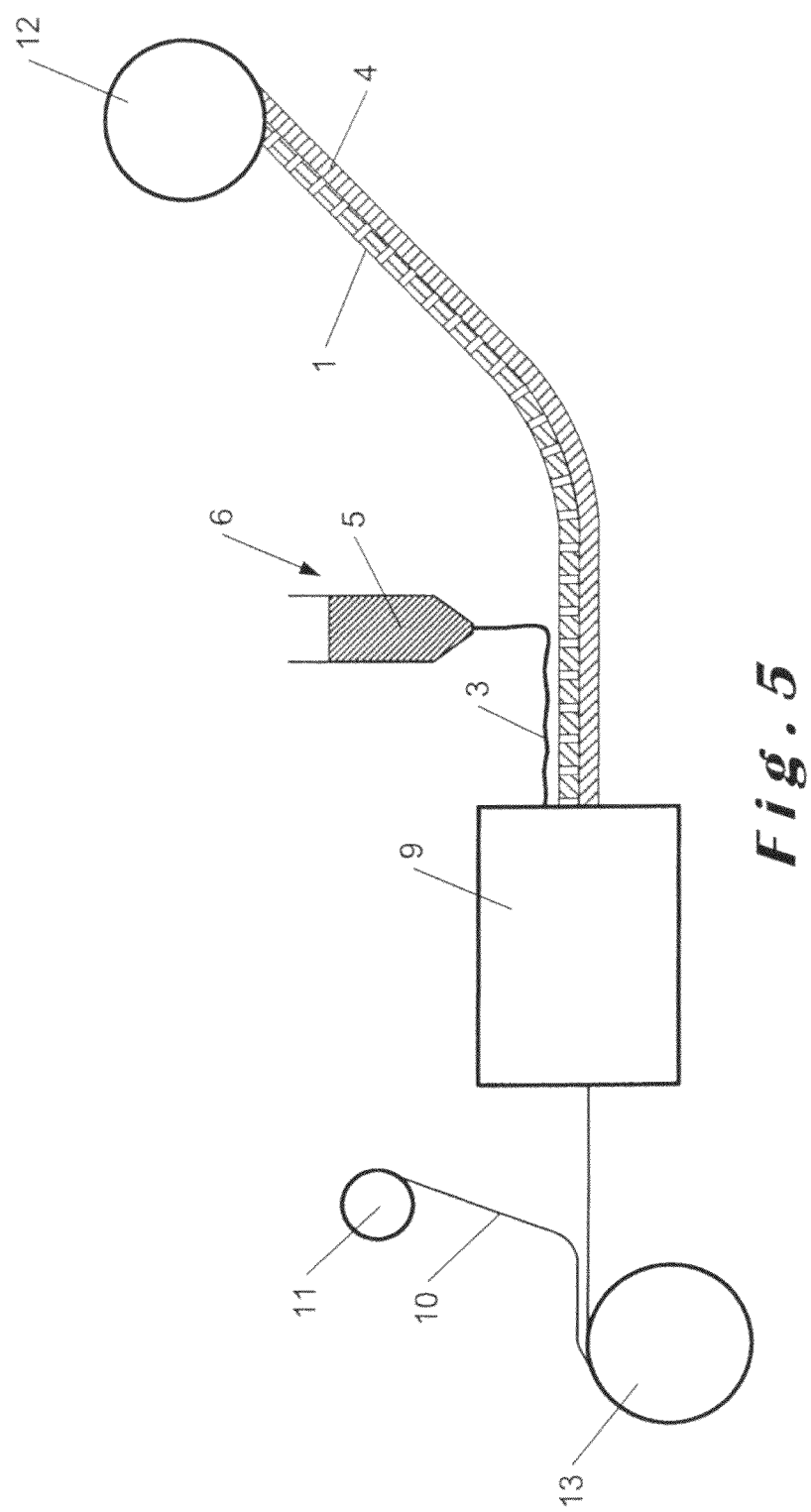

Each of these techniques will be explained in more detail in the following disclosure referring to the attached drawings in which FIG. 1 is a schematic representation of a first embodiment of the manufacture of an adhesive sheet material according to the invention, using a "transfer method";

FIG. 2 is a schematic representation of another embodiment of the manufacture of an adhesive sheet material according to the invention, using a "transfer method";

FIGS. 3 and 4 schematically illustrate the concept of forming apertures in a continuous adhesive coating layer obtained by a transfer method, by preferential adhesion of the adhesive to the carrier at the spot of the apertures;

FIG. 5 is a schematic representation of the manufacture of an adhesive sheet material according to the invention, using a "direct method"

Figure 6:
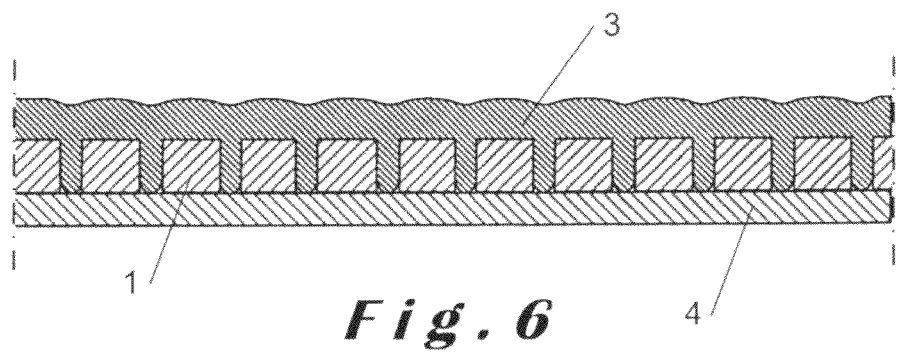
Figure 7:
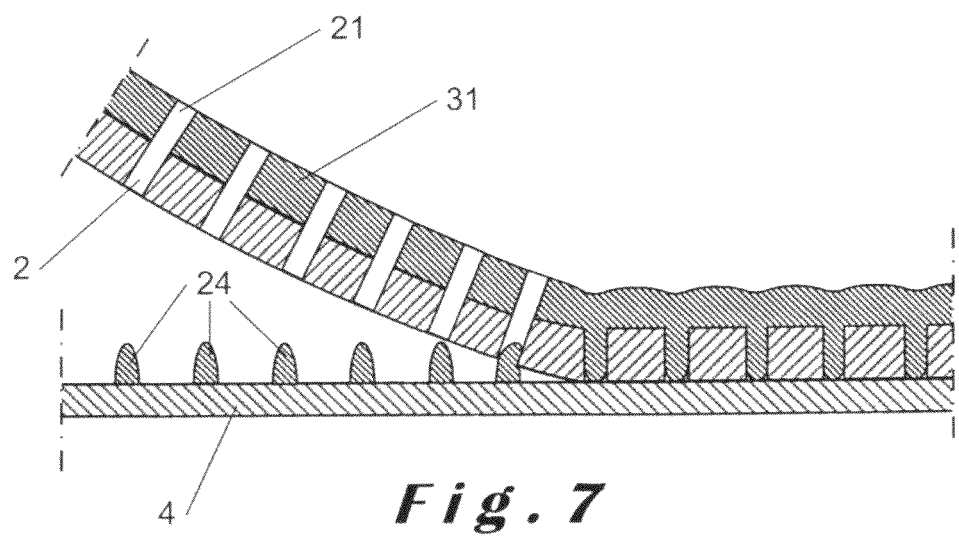

FIGS. 6 and 7 schematically illustrate the concept of forming apertures in a continuous adhesive coating layer obtained by a direct method, by preferential adhesion of the adhesive to the carrier at the spot of the apertures.

In all these figures corresponding elements/features are designated with the same or similar reference numerals.

A first embodiment—as illustrated in FIG. 1—of the "transfer method" variant of the process according to the invention, for manufacturing an adhesive sheet material comprising a sheet layer (designated with reference numeral 1) having apertures (designated with reference numeral 2) and an adhesive coating layer (designated with reference numeral 3) with apertures corresponding to at least part of the apertures of said sheet layer, respectively a composite sheet material comprising a sheet layer (1) having apertures (2), an adhesive coating layer (3) on said sheet layer having apertures, and a removable protective sheet layer (4) adhering at least partially to said adhesive coating layer (3), involves applying a liquid or pasty uncured adhesive composition/ mixture/compound (5), such as a therapeutic silicone gel (in particular a silicone gel composition distributed as Elastosil P7010), as a continuous layer (3) on the protective sheet layer (4), such as a specifically prepared transfer "paper" (consisting of paper or "plastic" material) acting as carrier, having a "thickness" of approximately 74 g/m², by using any technique or device (6) for applying liquid curing systems (5), as in themselves well known in the art.

In the specific example disclosed here the layer of adhesive coating is more in particular applied with a preferred "thickness" of approximately 100-240 g/m².

Subsequently the sheet layer (1), being any breathable sheet layer such as (knitted, woven or non woven) elastic fabric materials, "plastic netz" materials, "punctured", "perforated" or "apertured" plastic films, sheets of polymeric foam with open cells, perforated or non perforated breathable polyurethane sheet materials, etc., is applied and pressed onto the still "wet" (uncured) adhesive coating layer (3), using a calendering roll (7) with controlled pressure (8).

Immediately thereafter the composite/laminate is passed through an oven (not represented in the embodiment shown in FIG. 1) with drying air in the range of 60-200° C.

Using lower temperatures for the curing step requires longer curing times/longer curing ovens, which may involve a risk of having the uncured adhesive composition to "pass through" to the other side of the sheet layer (1), which is not desirable.

An optional further protective sheet layer (10) may be applied from a distribution roll (11) on the second side of the sheet layer (1) remote from the protective sheet (4), either before or after passing through the curing oven.

The composite/laminate is finally post-cured by passing over a heated metal roll (not represented), cooled and taken up on a roll (roll (13) not represented in FIG. 1).

A second embodiment—as illustrated in FIG. 2—of the "transfer method" variant of the process according to the invention for manufacturing an adhesive sheet material, respectively a composite sheet material, differs from the first embodiment as illustrated in FIG. 1 in that the sheet layer (1) having apertures (2), consisting more specifically of a particularly thin breathable sheet layer (such as a breathable polyurethane film), is fed into the coating installation together with a support sheet 10a (from a roll (12) not represented in FIG. 2), which may be removed and rolled up on a collecting roll 11a once the protective sheet (4) with the adhesive coating layer (3) have been applied and provide proper support to said particularly thin sheet layer (1).

The concept of forming apertures in the continuous adhesive coating layer (3) obtained by a transfer method as disclosed here above, is illustrated in FIGS. 3 and 4.

Due to the preferential adhesion of the adhesive layer (3) to the sheet layer material (1) with respect to the adhesion of the adhesive layer to the protective sheet (4) at the spot of the apertures, and the preferential adhesion of the adhesive layer to the protective sheet (4) with respect to the inherent internal cohesion of the cured continuous coating layer, portions (24) of the adhesive layer will, upon removal of the protective sheet (4), separate from the continuous adhesive layer and remain adhered to the protective sheet (4), leaving apertures (21) in the coating layer corresponding to the apertures (2) in the sheet layer (1).

The "direct method"—as illustrated in FIG. 5—of the process according to the invention for manufacturing an adhesive sheet, respectively a composite sheet material, differs from the methods as illustrated in FIGS. 1 and 2 in that the sheet layer (1) having apertures (2) is fed into the coating installation together with the protective sheet layer (4), from a supply roll (12), and in that the liquid or pasty uncured adhesive composition/mixture/compound (5), is applied directly onto the sheet layer (1) on the side remote from the protective sheet layer (4), as a continuous layer (3).

In this specific example the layer of adhesive coating is more in particular applied with a preferred "thickness" between 10 and 200 g/m².

Immediately thereafter the composite/laminate is passed through an oven (9).

A further protective sheet layer (10) is then applied, from a distribution roll (11) on the adhesive coating layer (3). The composite/laminate is finally post-cured by passing over a heated metal roll (not represented), cooled and taken up on a roll (13).

The concept of forming the apertures in the continuous adhesive coating layer (3) obtained by a direct method is illustrated in FIGS. 6 and 7.

Due to the preferential adhesion of the adhesive layer (3) to the protective sheet (4) with respect to the inherent internal cohesion of the cured continuous coating layer, portions (24) of the adhesive layer will, upon removal of the protective sheet (4), separate from the continuous adhesive layer and remain adhered to the protective sheet (4), leaving apertures (21) in the coating layer (31) on the adhesive sheet material corresponding to the apertures (2) in the sheet layer (1).

The invention has been disclosed here above in respect of its essential features as required for a skilled art person to be able to put the invention to practice.

Many variants to the invention will be readily apparent to the skilled art person, beyond the specific features and details set forth in this disclosure, without departing from the basic concept of the invention.

Thus in particular the method for applying the adhesive coating layer on the sheet layer having apertures may be carried out in one or more stages, optionally using well known techniques for applying a multi layer system of a substrate.

Appropriate further properties may also be provided to the adhesive sheet materials according to the invention, by an appropriate treatment of and/or incorporation of appropriate ingredients into the (constituent parts) of the used sheet layer material and or adhesive layer material.

This may for instance be achieved by applying nanotechnology means.

The fabric may be treated to provide it with anti-bacterial properties to the or nanocapsules may be added.

It is also possible to add nanocapsules to the adhesive coating layer to provide skin care properties to the protective accessory (using medical, homeopathic, pharmaceutical or cosmetic preparations).

The following (non limiting) examples serve to further illustrate the invention.

EXAMPLE 1

A bi-elastic warp knitted eyelet fabric comprising

23% of elasthane fibers (Lycra®) and

77% of polyester fibers, showing 300 apertures/dm², with a thickness of 0.5 mm and a specific weight of 185 g/m² was produced on a jersey type knitting machine with two eyelet beams ("tricotmachine met 2 ogenbalken" in Dutch), using "net-laying" ("Filet-Legung" in German).

The applied pattern ratio was 20 rows, with on eyelet beam 1:

6 rows closed stitch jersey ("*gesloten steek tricot*" in Dutch) +

4 rows atlas open stitch to the right + 6 rows closed stitch jersey +

4 rows atlas open stitch to the left, and on eyelet beam 2:

6 rows closed stitch jersey + 4 rows atlas open stitch to the left +

6 rows closed stitch jersey + 4 rows atlas open stitch to the right;

So, in other words the two eyelet beams produce the same pattern but with a shift of 10 rows;
the applied "pull trough" was 3 full and 1 empty;

The elastic warp knitted eyelet fabric shows approximately 300-350 eyelets/dm$^2$ (in fact ~325 eyelets/dm$^2$), with an eyelet opening area of approximately 10% (in fact ~9.75%) of the sheet fabric area.

This fabric was provided with a coating layer of a two component silicone system (ELASTOSYL® P 7010 from WACKER),
using transfer technology, so as to achieve a cured coating layer of silicone gel, with a thickness of 300μ and a weight of 200 g/m$^2$, on the fabric layer, in such way that (once cured) the silicone system material corresponding to the apertures in the fabric layer remain on the back of the transfer sheet (highly smooth paper-like backing sheet), which latter also acts as a (removable and reusable) protective sheet for the tacky gel layer of the composite sheet material.

The obtained adhesive sheet material (namely the composite sheet material without protective sheet, i.e. with its protective sheet removed) shows
- a thickness of 0.8 mm and a specific weight of 385 g/m$^2$,
- a moisture vapour transmission rate (according to ASTM E96) of 2440 g/m$^2$/day
- an air permeability (according to ISO 9237.2) 825 l/(m$^2$·s).

EXAMPLE 2

A breathing polyurethane film (commercial medical grade film with a thickness of approximately 150μ, having a moisture vapour transmission rate of approximately 1000 g/m$^2$/24 h) of approximately 35 g/m$^2$, provided with a protective paper sheet layer having a "thickness" of approximately 75 g/m$^2$, was provided (on laboratory scale) with a coating layer of ELASTOSYL® P 7010, using the "direct method" as referred to above, with the uncured silicone gel mixture applied at a coating thickness of 120 g/m$^2$, to the PU film side remote from the protective paper layer.

The composite sheet consisting of adhesive coating/PU film/plastic protection foil was cured for 5 minutes at approximately 150° C.° in an oven, after which a plastic protection foil of approximately 40 g/m$^2$ was provided onto the cured adhesive coating layer.

The product showed excellent skin adhesion/skin release properties and an exceptional reusability (several adhesion/release cycles, even after intermediate washing of the adhesive film).

The invention claimed is:

1. A composite sheet material comprising a sheet layer having apertures, a continuous cured adhesive coating layer on said sheet layer; and a removable protective sheet layer adhering at least partially to said adhesive coating layer, wherein said adhesive coating layer shows a first adherence capacity $A_1$ towards the protective sheet layer and a second adherence capacity $A_2$ towards the sheet layer having apertures, said second adherence capacity $A_2$ being greater than said first adherence capacity $A_1$; the respective layers being arranged such that upon removal of said protective sheet layer, a portion of said adhesive coating layer remains on said protective sheet layer and the portion of said adhesive coating layer remaining adhered to said sheet layer includes apertures therein corresponding to at least a portion of the apertures of said sheet layer.

2. The composite sheet material of claim 1, wherein said adhesive layer has a thickness between 50 μm and 1000 μm.

3. The composite sheet material of claim 1, wherein said adhesive layer has a thickness between 100 μm and 500 μm.

4. The composite sheet material of claim 1, wherein said protective sheet layer has a thickness ranging from about 0.01 mm to about 2 mm.

5. The composite sheet material of according to claim 1, wherein said protective sheet layer has a thickness ranging from about from 0.02 mm to 0.6 mm.

6. The composite sheet material of claim 1 wherein said protective sheet material has a thickness ranging from 0.05 mm to about 1 mm.

7. The composite sheet material of claim 1 wherein said protective sheet material has a thickness ranging from 0.1 to 0.6 mm.

8. The composite sheet material of claim 1 wherein said adhesive layer is present on said sheet layer at a ratio of 10 to 500 g/m$^2$.

9. The composite sheet material of claim 1 wherein said adhesive layer is present on said sheet layer at a ratio of 10 to 300 g/m$^2$.

10. A method for manufacturing a sheet material comprising:
   applying a continuous layer of uncured adhesive material to a layer of protective sheet material,
   applying a sheet layer having apertures therein onto said continuous layer of uncured adhesive material to form a composite; and
   submitting said composite to a curing operation for said adhesive material wherein, said adhesive material, when cured, and said protective sheet material show a first adherence capacity $A_1$ towards each other, and said sheet layer having apertures and said adhesive material, when cured, show a second adherence capacity $A_2$ towards each other, said second adherence capacity $A_2$ being greater than said first adherence capacity $A_1$.

11. The method of claim 10 wherein said uncured adhesive material extends into said apertures of said sheet layer.

12. The method of claim 10 wherein said curing operation causes said layer of adhesive material to preferentially adhere to said area of the sheet layer which does not contain apertures.

* * * * *